US008545390B2

(12) United States Patent
Talbot et al.

(10) Patent No.: US 8,545,390 B2
(45) Date of Patent: Oct. 1, 2013

(54) SEXUAL STIMULATION DEVICE

(75) Inventors: Nicholas C. Talbot, London (GB); Ketan Mistry, Middlesex (GB); Sean J. Tasker, Manchester (GB)

(73) Assignee: LRC Products Limited, Slough, Berkshire (GB)

( * ) Notice: Subject to any disclaimer, the term of this patent is extended or adjusted under 35 U.S.C. 154(b) by 1063 days.

(21) Appl. No.: 12/309,073

(22) PCT Filed: May 7, 2007

(86) PCT No.: PCT/GB2007/002509

§ 371 (c)(1), (2), (4) Date: Aug. 5, 2009

(87) PCT Pub. No.: WO2008/003969

PCT Pub. Date: Jan. 10, 2008

(65) Prior Publication Data

US 2010/0010292 A1 Jan. 14, 2010

(30) Foreign Application Priority Data

Jul. 6, 2006 (GB) .................................. 0613455.5

(51) Int. Cl.
*A61F 5/00* (2006.01)

(52) U.S. Cl.
USPC ............................................................ 600/38

(58) Field of Classification Search
USPC ..................................................... 600/38–41
See application file for complete search history.

(56) References Cited

U.S. PATENT DOCUMENTS

| | | | | |
|---|---|---|---|---|
| 4,643,175 | A * | 2/1987 | Chapman | 600/38 |
| 6,907,883 | B2 | 6/2005 | Lin | |
| 6,991,600 | B1 | 1/2006 | Wang | |
| 2002/0103415 | A1 | 8/2002 | Manska et al. | |
| 2003/0083598 | A1 | 5/2003 | Kobayashi et al. | |
| 2003/0181835 | A1 * | 9/2003 | Klein | 601/72 |
| 2004/0242957 | A1 * | 12/2004 | Ward | 600/39 |
| 2005/0081863 | A1 | 4/2005 | Lin | |
| 2006/0178602 | A1 * | 8/2006 | Teng et al. | 601/70 |
| 2007/0038019 | A1 * | 2/2007 | Weng | 600/38 |

FOREIGN PATENT DOCUMENTS

| | | |
|---|---|---|
| DE | 2310430 | 9/1974 |
| DE | 20311823 | 10/2003 |

OTHER PUBLICATIONS

The Xandria Collection Catalog, Oct. 20, 2000 p. 8 and cover "The Clitoral Kiss".*
English Abstract of DE20311823.

* cited by examiner

*Primary Examiner* — Samuel Gilbert
(74) *Attorney, Agent, or Firm* — Ryan A. Schneider; Troutman Sanders LLP

(57) ABSTRACT

A sexual stimulation device comprises a casing (2) in which is contained a vibrator unit and connection means in the form of gripping limbs (6, 7) for holding the device to the penis. The connection means extend about the penis in a connection place (P) and a longitudinal axis (c) of the casing (2) is inclined to the connection plane (P) whereby, in use, the casing (2) extends along and away from the penis.

13 Claims, 6 Drawing Sheets

SEXUAL STIMULATION DEVICE

The present invention relates to sexual stimulation devices.

In the prior art various sexual stimulation devices are known. For example, so-called electric condom rings comprise an elastic ring for fitting over the penis, with an electric vibrating device connected to the ring. A switch is provided to turn on and off the vibrating device.

GB2414938 discloses an electric condom ring wherein the elastic ring comprises a resilient loop with a pair of constrictions, which act as weak points to allow the device to be broken off if necessary. Once the resilient loop has been broken, the condom ring cannot be re-used. The electric vibrating device is connected to the resilient loop in a tangential orientation, and has a protrusion for stimulating the clitoris.

The present invention provides a sexual stimulation device comprising a casing having a vibrator unit disposed therein, the vibrator unit comprising an electric motor provided with a rotatably driveable eccentric mass whereby operation of the electric motor produces vibrations, and resiliently flexible gripping means connected to the casing for embracing a penis to connect the device to the penis, wherein the gripping means includes a discontinuity.

Due to the inclusion of the discontinuity a user of the device is able to remove the device from the penis during sexual intercourse, without requiring the penis to be withdrawn or the gripping means to be broken. The device is thus not prevented from being re-used. Further, the device can be re-connected to the penis during intercourse without requiring withdrawal.

Preferably, the gripping means comprise first and second limbs, preferably of substantially equal length, with the discontinuity situated between free ends of the limbs. Advantageously, a portion of each limb distal to the casing can be broader than a proximal region of the limb, whereby a secure, stable connection of the device to the penis is facilitated.

One or more ridges may be provided on the casing for stimulating the clitoris, and in particular they may emanate from a common region on the exterior surface of the casing.

Preferably, the vibrator unit comprises a housing in which the electric motor and the eccentric mass are situated, a battery being disposed in the housing for providing power to the electric motor, an electrical conductor connecting a pole of the battery to a first electrode of the electric motor and a switch connecting the other pole of the battery to a second electrode of the electric motor wherein the switch comprises a bi stable actuating means pushable in one direction to switch on the electric motor and pushable in the same direction to switch off the electric motor.

It is thereby particularly simple to operate the switch, as the user merely has to press the actuating means to turn the device on, and press again to turn the device off. The actuating means can advantageously be positioned on the device so as to avoid accidental switching on of the device. By virtue of the actuating means turning the vibrator unit on and off by pressing in the same direction, it is advantageously provided that if the device is accidentally switched on it is more likely than the prior art devices to be accidentally switched off again. By virtue of disposing the vibrator unit in the casing, the vibrator unit is protected from fluids thereby helping to prevent short circuiting within the vibrator unit, and the device is thus also hygienic.

Advantageously the actuating means of the switch can be situated towards a side of the vibrator unit which in use faces away from the penis whereby the actuating means is unlikely to be accidentally knocked during use. This helps to prevent inadvertent turning on or off of the device during use.

In a second aspect of the invention there is provided a sexual stimulation device comprising a casing having a vibrator unit disposed therein to extend along a longitudinal axis of the casing, the vibrator unit comprising an electric motor provided with a rotatably driveable eccentric mass whereby operation of the electric motor produces vibrations, and connection means connected to the casing adjacent an end of the casing for connecting the device to a penis, the connection means being arranged to extend about the penis in a connection plane, and the longitudinal axis of the casing being inclined to the connection plane whereby, in use, the longitudinal axis of the casing extends forwardly along and away from the penis for the casing to contact the clitoris.

Advantageously, by virtue of the inclined orientation of the casing with respect to the penis, the casing makes particularly effective engagement with the clitoris, which engagement is more prolonged than with the prior art devices, since the casing has a tendency over the range of motion of the penis with respect to the vagina, to provide a degree of rubbing of the clitoris, rather than the simple nudging motion that may be expected from the prior art devices.

Preferably, the longitudinal axis of the casing is generally perpendicular to the connection means in the region of the connection between the casing and the connection means. In this way, the casing, in use, points towards the clitoris.

Advantageously, the eccentric mass can be situated at an end of the casing distal from the connection means, whereby the vibrations are more pronounced at that end of the casing.

In accordance with either aspect of the invention, the sexual stimulation device can comprise a self-contained apparatus, without a plurality of separate parts requiring complex operation procedures to be used.

There now follows a detailed description of embodiments of the invention by way of example with reference to the accompanying drawings, in which FIG. 1 is a rear elevation of a sexual stimulation device according to the invention;

FIG. 7 shows the contents of the vibrator unit with the switch turned on;

Figure 1:
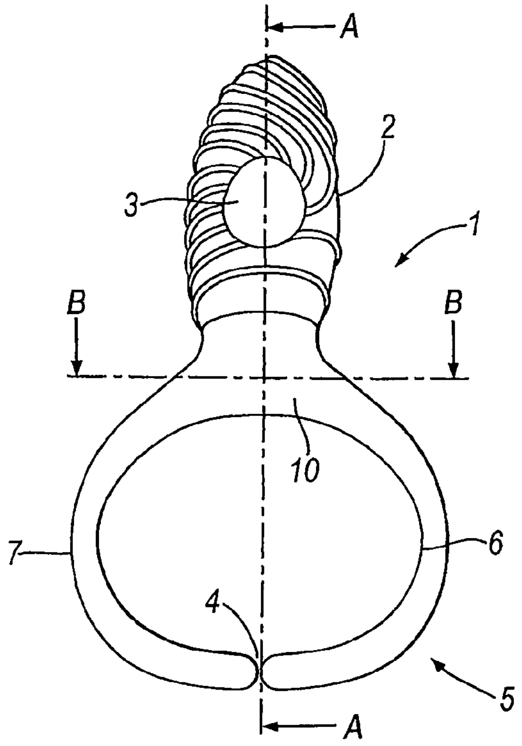

The sexual stimulation device 1 illustrated in FIGS. 1 to 4 comprises a casing 2 made of a flexible rubber material, defining a resilient sleeve. A vibrator unit is located inside the casing 2. On an upper side of the casing, directly opposite a side of the casing which in use faces the penis, is an on/off push button 3. The button 3 is lozenge-shaped and comprises a resiliently compressible sealing element, which may optionally be sealed to the vibrator unit within the casing 2, so as to be waterproof. Alternatively, the seal may be water resistant. The casing 2 defines a hole through which the button 3 protrudes, though not necessarily all the way through the hole. Thus, the casing covers all of the vibrator unit apart from the button 3 of the vibrator unit. In manufacture, the vibrator unit is inserted into the casing through the hole. As an alternative, the casing 2 and the button 3 could be integral whereby a watertight seal would be guaranteed. This would require a different method of disposing the vibrator unit in the casing 2, e.g. moulding the casing around the vibrator unit.

Connection means 5 are connected to the casing 2 and comprise resiliently flexible gripping means 5 in the form of first and second limbs 6, 7. A discontinuity 4, formed as a break in the material of the gripping means, separates the gripping means 5 into the first and second limbs 6, 7 which are symmetrical with each other. The discontinuity 4 is situated between the free ends of the limbs 6, 7 distal from the casing. With this structure, the device can be very quickly and easily removed from the penis by pulling it upwards. It would, however, also be possible to have the discontinuity situated towards the side of the gripping means, whereby the device can be pulled off sideways. The limbs 6, 7 as shown are symmetrical relative to the casing, i.e. about the line A-A. The ends of the limbs 6, 7 have a small gap therebetween, but alternatively could be touching one another. The pair of limbs 6, 7 is configured to embrace the penis in a connection plane P. By virtue of the resilience of the gripping limbs, they will reliably return to their non-use position when not embracing the penis.

The limbs 6, 7 include free end portions 8 distal from the casing that are broader than proximal end regions 9 of the limbs. An inner peripheral surface of each limb 6, 7 is generally flat or cylindrical, thereby defining a partial sheath around the penis. By virtue of extending along the length of the penis to some degree, the limbs 6, 7 provide a stable and secure connection of the device to the penis. The limbs 6, 7 are curved with respect to the connection plane P so that the distal portions 8 of the limbs 6, 7 point to some extent forwardly along the penis, which again stabilises the device.

A vibrator unit 40 is disposed inside the casing 2. The casing 2 is generally shaped as a prolate spheroid, except in the region where the gripping limbs 6, 7 meet the casing 2. Ridges 11 protrude from the casing 2 and are arranged in a series of swirls, each ridge 11 looping back on itself, and many of the ridges 11 emanating from the button 3. The layout of the ridges 11 is aesthetically appealing and helps to stimulate the clitoris.

Figure 2:
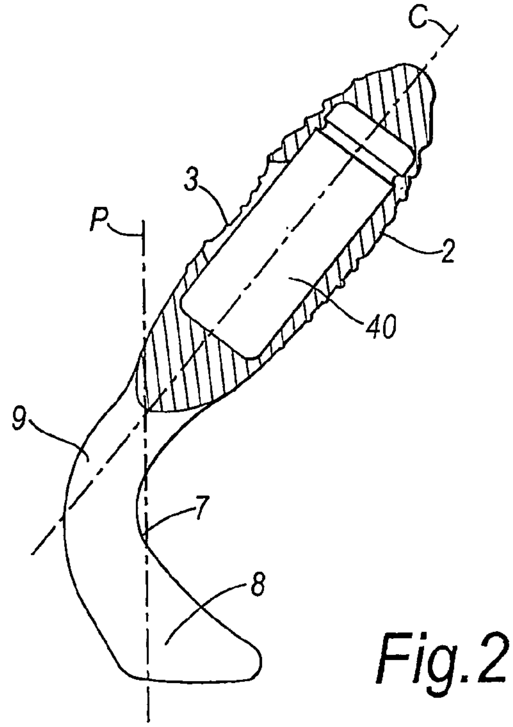
FIG. 2 is a cross-section along the line A-A through the device of FIG. 1.
Figure 3:
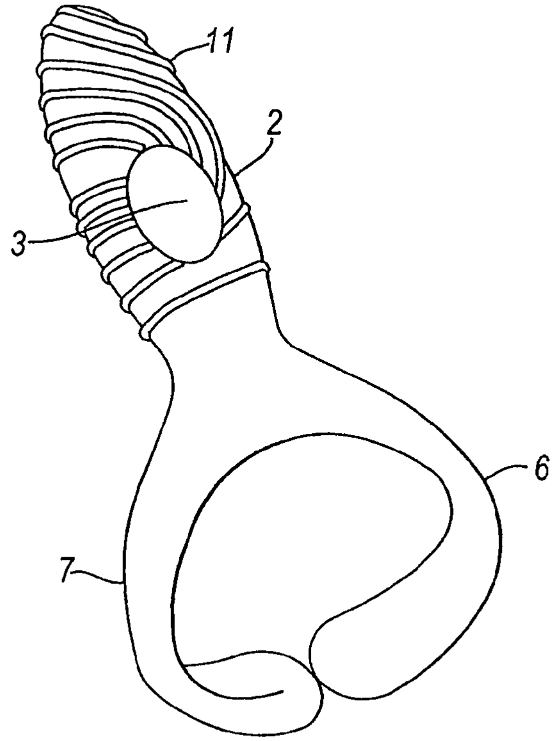
FIG. 3 is a rear perspective view of the device of FIG. 1.
Figure 4:
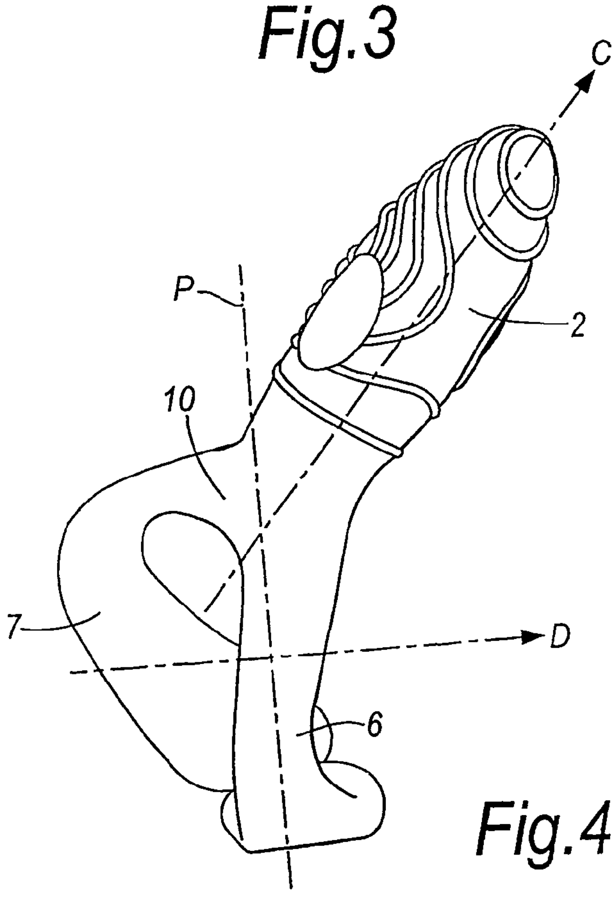
FIG. 4 is a side perspective view of the device of FIG. 1.

The casing has a longitudinal axis C, as represented by a dashed line in FIGS. 2 and 4, which is generally perpendicular to the limbs 6, 7 in the region 10 of the connection between the casing 2 and the limbs 6, 7. Referring to FIG. 1, the casing can be seen to be perpendicular to a line B-B at the connection region 10. Furthermore, the longitudinal axis C of the casing is inclined to the connection plane P. The casing 2, when the device is correctly placed on the penis, thus aligns with and engages effectively with the clitoris.

A dashed line D shown in FIG. 4 represents the orientation of the penis with respect to the device in use, i.e. essentially perpendicular to the connection plane P. With the connection plane defined by the limbs 6, 7 inclined relative to the longitudinal axis C of the casing 2, in use the longitudinal axis of the casing points forwardly and upwardly, i.e. along and away from the penis.

The angle of inclination of the longitudinal axis C of the casing with respect to the connection plane can lie in the range 20° to 45°.

Figure 5:
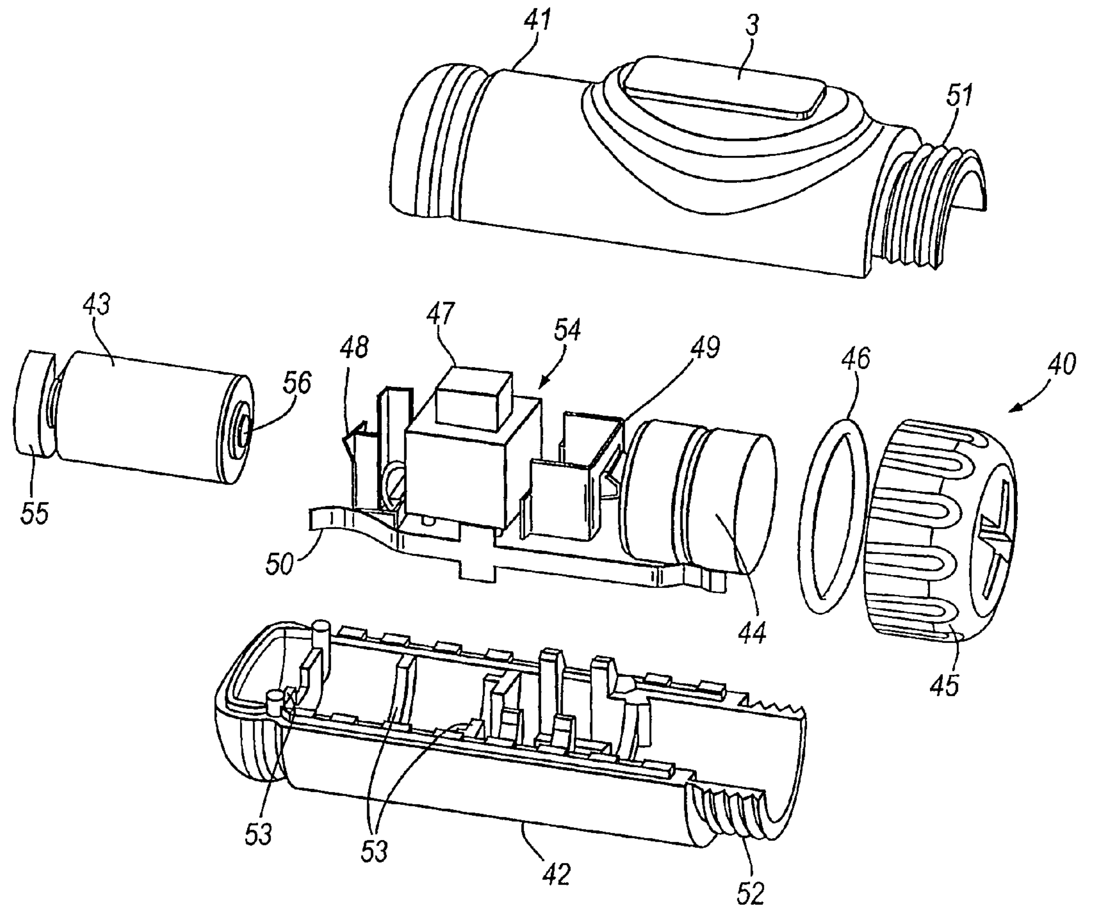
FIG. 5 is an exploded view of a vibrator unit used in the device shown in FIG. 1.

The vibrator unit 40 which is illustrated in exploded form in FIG. 5, comprises a housing assembled from first and second generally semi-cylindrical half shells 41 and 42. At least one of the half shells 41, 42 includes internal ribs 53 which serve to hold the contents of the housing in place. The half shells 41, 42 include respective threaded portions 51, 52 at an end thereof arranged such that when the half shells 41, 42 are brought together the threaded portions 51, 52 define a threaded tubular connector to which an end-cap, e.g. a screw-cap 45 is attachable and may serve to hold the shells 41, 42 together. Alternatively, or additionally, the housing half shells 41, 42 may snap-fit together. On top of the first half shell 41, the operating button 3 is located.

The components accommodated inside the housing 41, 42 are an electric motor 43, a switch 54 and one or more batteries 44 (in the present embodiment, two batteries), as well as various electrical contacts. The electric motor has an eccentric mass 55 connected to its output drive shaft whereby operation of the electric motor produces vibrations. An electrical conductor 50 comprising an elongate metallic strip connects a first electrode of the electric motor, the first electrode comprising a side of a metallic housing of the motor 43, to a pole of the battery 44 formed by a side of a metallic casing of the battery. Situated in a cavity defined between the electric motor and the battery is a switch 54 for switching the electric motor 43 on and off. The switch 54 includes bi-stable actuating means 47 comprising a push-button 47 which is depressed by the user to operate the switch to turn on the electric motor 43. To switch off the electric motor 43, the user depresses the push-button 47 again. In practice, of course, the user depresses the resilient rubber button 3 on the vibrator unit housing, which is situated directly adjacent to the push-button 47. On either side of the switch 54, there are provided first and second contact means 48, 49 comprising first and second metallic contact plates. The first metallic plate 48 establishes an electrical connection between a pole 54 of the electric motor situated on a longitudinal end face of the electric motor, and a first terminal 61 of the switch (see FIG. 5), whereas the second metallic contact plate 49 establishes an electrical connection between a pole of the battery 44 defined by an end face of the battery 44 and a second terminal 62 of the switch 54. The primary purpose of the metallic plates 48, 49 is to adapt the switch 54 which is a standardised component, to the particular application in hand. The metallic plates 48, 49 may include contacting portions which are resiliently biased against the components with which they are in contact to provide a good electrical connection. An O-ring 46 is disposed around the threaded tubular connector formed by the two housing shells 41, 42, serving to seal the connection between the housing and the screw-cap 45. An annular groove extends around the housing adjacent the end opposite the cap 45 and may receive a rib moulded on the inside of the casing to assist location of the vibrator unit within the outer casing.

Figure 6:
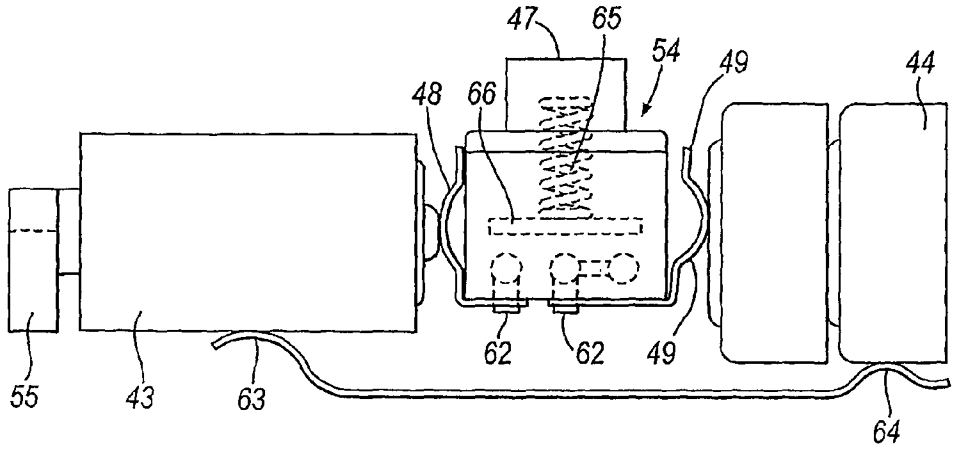
FIG. 6 shows the contents of the vibrator unit with a switch turned off.
Figure 7:
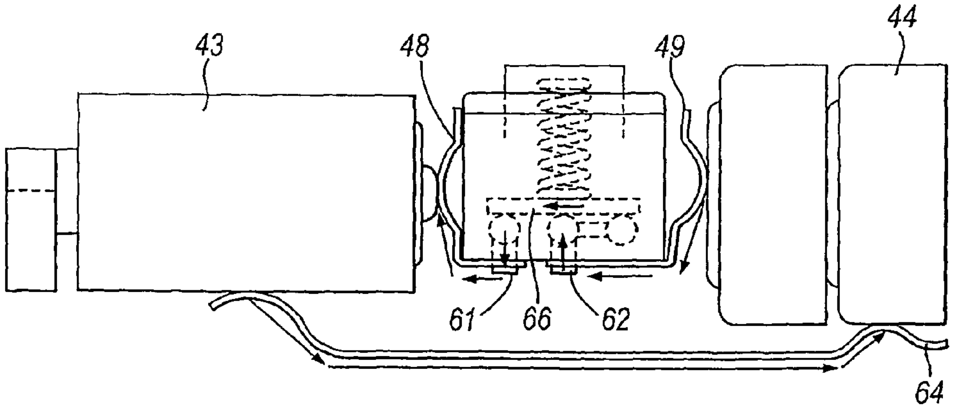

The inner working components of the vibrator unit are shown assembled together in FIGS. 6 and 7, with the switch 54 being in the "off" state in FIG. 6 and in the "on" state in FIG. 7. The actuating button 47 of the switch 54 is connected by a spring 65 to an electrically conductive switch plate 66 which is movable to a position bridging a gap between two contact terminals 61 and 62, illustrated in FIG. 7, thereby completing the circuit for switching on the electric motor. Inside the switch are latching means for making the actuating button 47 bi-stable, so that the switch remains in the on condition until the actuating button is depressed again so that the switch contact plate 66 returns to the "off" position of FIG. 6. The electrical conductor 50 has a first curved portion for contacting the side of the electric motor 43 and a second curved portion 64 for contacting the side of the battery 44.

Figure 8:
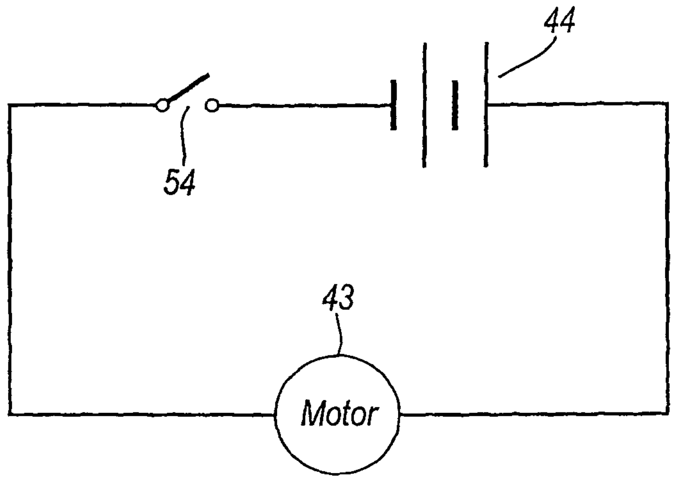
FIG. 8 shows a simplified schematic circuit diagram of the vibrator unit.

FIG. 8 is a simple circuit diagram showing schematically the electrical connections between the switch 54, the battery 44 and the electric motor 43. In the present embodiment the two batteries 44 are connected in series, but it would also be possible to connect the batteries in parallel with one another to produce vibrations of a lower power. In this regard, the internal components of the vibrator unit can be arranged to allow the user to choose between a series connection or a parallel connection of the batteries, e.g. by pressing the push button 3.

Figure 9:
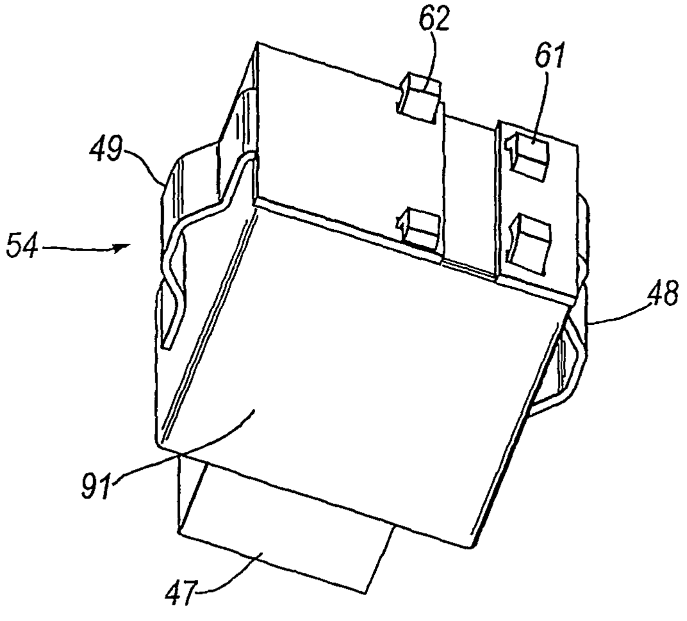
FIG. 9 shows in perspective the switch used in the vibrator unit.

FIG. 9 shows a detail of the switch 54, including the first and second contact plates 48, 49 (in a slightly different configuration to that shown in FIG. 5), the electrical terminals 61, 62 and the actuating means 47. The housing of the switch is made from plastics material whereas the contact plates and terminals are metallic.

Figure 10:
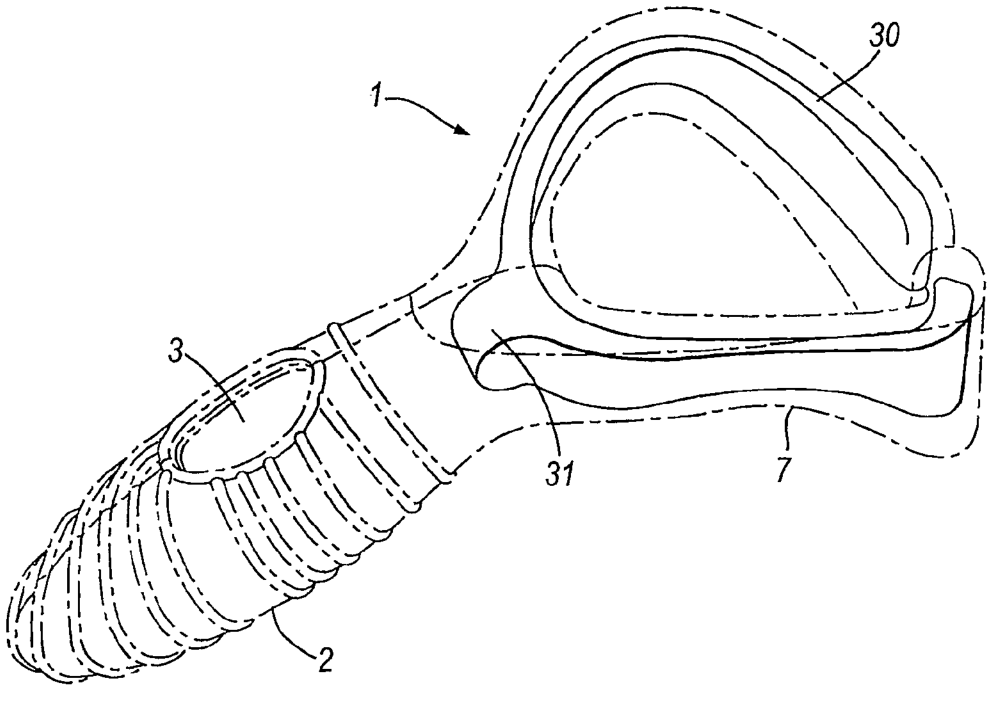
FIG. 10 shows in perspective a preferred embodiment of a device according to the invention.

FIG. 10 shows a preferred form of the sexual stimulation device 1 shown in FIGS. 1 to 4, which includes a resilient element 30, e.g. in the form of a bracket, engaged with the gripping means 7 to provide a gripping force. The resilient element 30 improves the stability of the device when placed on the penis, by providing an increased gripping force, and thereby reduces the potential for the device to rotate around the penis or to slip off during use. The increased gripping force may also assist in the maintenance of an erect state of the penis by causing blood to be retained therein. In the preferred embodiment, the resilient element 30 is situated inside the device and, in particular, the casing 2 and/or gripping means 7 of the device 1 can be moulded around the resilient element 30. This ensures a sturdy integration of the resilient element 30 within the device 1 and allows the device to be manufactured with a simple and convenient process. The resilient element has a portion 31 having a thicker cross-section than other parts of the resilient element, and this can lend extra resilience to the gripping means. Although FIG. 10 shows a unitary resilient element 30, it is also possible to have more than one resilient element. For example, an individual resilient element could be provided in each gripping limb.

The resilient element comprises a material having a flexural modulus in a range of approximately 2000 to 2500 MPa. This range of values is believed to provide an optimal strength of gripping force which is sufficient to hold the device in place when in use without being so strong as to be uncomfortable to the user. Polycarbonate is one example of a material which can be used to make the resilient element 30, and in particular an unfilled polycarbonate may be used. Specifically, Calibre® 301V-10 polycarbonate resin is used, having a flexural modulus of 2,410 MPa.

With regard to the materials used to manufacture the casing 2 and the gripping means 7 of the device 1, a material with a Shore A hardness in the range of approximately 15 to 35 is preferred. One type of material which may be used is a hydrogenated styrene isoprene/butadiene block copolymer. Any other thermoplastic rubber or elastomer with a hardness around this range of values would be suitable, so long as it is appropriate for injection moulding. The particular preferred material is Septon® 4033, having a Shore A hardness of 25.

The invention claimed is:

1. A sexual stimulation device comprising a casing having a vibrator unit disposed therein to extend along a longitudinal axis of the casing, the vibrator unit comprising an electric motor provided with a rotatably drivable eccentric mass whereby operation of the electric motor produces vibrations, and connection means connected to the casing adjacent an end of the casing for connecting the device to a penis, the connection means being arranged to extend about the penis in a connection plane, and the longitudinal axis of the casing being inclined to the connection plane whereby, in use, the longitudinal axis of the casing extends forwardly along and away from the penis for the casing to contact the clitoris, wherein the connection means comprises gripping means which includes a discontinuity, and further comprising at least one resilient element engaged with the gripping means to provide a gripping force.

2. The device according to claim 1, wherein the longitudinal axis of the casing in use is disposed at an angle in the range of 20° to 45° to the connection plane.

3. The device according to claim 2, wherein the longitudinal axis of the casing is generally perpendicular to adjoining parts of the connection means in the region of the connection between the casing and the connection means.

4. The device according to claim 3, wherein an exterior surface of the casing is provided with a raised protrusion for stimulating the clitoris.

5. The device according to claim 4, wherein a plurality of ridges are provided on the exterior surface of the casing, and wherein at least some of the ridges emanate from a common region on the exterior surface of the casing.

6. The device according to claim 1, wherein the gripping means comprise first and second limbs, the discontinuity being situated between free ends of the limbs, wherein a portion of each limb distal from the casing is broader than a proximal region of the limb.

7. The device according to claim 6, wherein the gripping means and the casing are integrally formed.

8. A device according to claim 1, wherein the resilient element is located inside the gripping means and/or the casing.

9. The device according to claim 8, wherein the resilient element comprises a material having a flexural modulus in the range of approximately 2000 to 2500 MPa.

10. The device according to claim 9, wherein the casing and/or the connection means comprise a material having a Shore A hardness in the range of approximately 15 to 35.

11. The device according to claim 10, wherein the casing and/or the connection means comprise a hydrogenated styrene isoprene/butadiene block copolymer.

12. The device according to claim 11, wherein the vibrator unit comprises a housing in which the electric motor and the eccentric mass are situated, a battery in the housing for providing power to the electric motor, an electrical conductor connecting a pole of the battery to a first electrode of the electric motor and a switch connecting the other pole of the battery to a second electrode of the electric motor wherein the switch comprises bi-stable actuating means pushable in one direction to switch on the electric motor and pushable in the same direction to switch off the electric motor, wherein the switch is situated in a cavity defined between the electric motor and the battery.

13. The device according to claim 12, wherein the actuating means of the switch is situated towards a side of the vibrator unit which in use faces away from the penis.

* * * * *

UNITED STATES PATENT AND TRADEMARK OFFICE

CERTIFICATE OF CORRECTION

PATENT NO. : 8,545,390 B2
APPLICATION NO. : 12/309073
DATED : October 1, 2013
INVENTOR(S) : Nicholas C. Talbot, Ketan Mistry and Sean J. Tasker It is certified that error appears in the above-identified patent and that said Letters Patent is hereby corrected as shown below:

Title Page, below Item (21) should read

-- (22) PCT Filed: July 5, 2007 --

Signed and Sealed this
Twenty-fourth Day of December, 2013

Margaret A. Focarino
*Commissioner for Patents of the United States Patent and Trademark Office*